(12) United States Patent
Krisch et al.

(10) Patent No.: US 7,632,843 B2
(45) Date of Patent: Dec. 15, 2009

(54) TREATMENT OF PSYCHOSTIMULANT ADDICTION

(75) Inventors: Igor Krisch, Ljubljana (SI); Marko Zivin, Ljubljana (SI); Natasa Milivojevic, Ljubljana (SI); Rudolf Rucman, Ljubljana-Smartno (SI); Breda Bole-Vunduk, Ljubljana (SI); Uros Urleb, Ljubljana (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 398 days.

(21) Appl. No.: 10/539,501

(22) PCT Filed: Dec. 11, 2003

(86) PCT No.: PCT/SI03/00045

§ 371 (c)(1),
(2), (4) Date: Sep. 2, 2005

(87) PCT Pub. No.: WO2004/054578

PCT Pub. Date: Jul. 1, 2004

(65) Prior Publication Data

US 2006/0014775 A1    Jan. 19, 2006

(30) Foreign Application Priority Data

Dec. 17, 2002  (SI) .............................. P-200200305

(51) Int. Cl.
| | |
|---|---|
| A61K 31/135 | (2006.01) |
| A61K 31/33 | (2006.01) |
| A61K 31/395 | (2006.01) |
| A61K 31/56 | (2006.01) |
| A61P 25/30 | (2006.01) |

(52) U.S. Cl. .................. 514/288; 514/337; 514/359; 514/646; 514/650; 514/655; 514/810

(58) Field of Classification Search .............. 514/288
See application file for complete search history.

(56) References Cited

U.S. PATENT DOCUMENTS

| | | | |
|---|---|---|---|
| 4,935,429 A | | 6/1990 | Dackis et al. |
| 5,430,031 A | | 7/1995 | Brambilla et al. |
| 5,441,961 A | | 8/1995 | Cohen et al. |
| 5,480,885 A | * | 1/1996 | Rucman et al. .............. 514/288 |

FOREIGN PATENT DOCUMENTS

WO        01/41763       6/2001

OTHER PUBLICATIONS

Smelson et al, "Risperidone Decreases Craving and Relapses in Individuals with Schizophrenia and Cocaine Dependence", Can J Psychiatry, vol. 47, No. 7, Sep. 2002.*
Pulvirenti et al., "Characterization of the Effects of the Partial Dopamine Agonist Terguride on Cocaine Self-Administration in the Rat", Journal of Pharmacology and Experimental Therapeutics, 1998, 286, pp. 1231-1238.*
Pulvirenti et al., Dopamine receptor agonists, partial agonists, and psychostimulant addiction, Trends Pharmacol Sci 1994, 15, pp. 374-379.*
L Handelsman et, al, Am J. Addict, vol. 6 (1) "Bromocriptine for Cocaine Dependence", A controlled clinical trial.
Milivojevic et al., "A Novel Ergoline Derivative LEK-8829 Attenuates Cocaine-Induced Reinstatement of Cocaine-Seeking Behavior", Behavioural Pharmacology, vol. 14, No. Suppl. 1, p. S55 (2003).
Glavan et al., "Modulation of Neuroleptic Activity of 9,10-didehydro-N-methyl-(2-propynyl)-6-methyl-8-aminomethylergoline bimaleinate (LEK-8829) by D1 Intrinsic Activity in Hemi-Parkinsonian Rates", Molecular Pharmacology, vol. 61, No. 2, pp. 360-368 (2002).
Zivin et al., "Antiparkinsonian Potential of Interaction of LEK-8829 with Bromocriptine", European Journal of Pharmacology, Vol. 349, No. 2-3, pp. 151-157 (1998).

* cited by examiner

*Primary Examiner*—Sreeni Padmanabhan
*Assistant Examiner*—Sahar Javanmard
(74) *Attorney, Agent, or Firm*—Luedeka, Neely & Graham, P.C.

(57) ABSTRACT

The present invention belongs to the field of pharmaceutical industry and relates to a new method for the treatment of psychostimulant addiction, in particular cocaine addiction, or pharmaceutically acceptable acid addition salts thereof, with a therapeutically effective amount of 9,10-didehydro-N-methyl-N-(2-propy-nyl)-6-methyl-8β-aminomethylergo-line in the form of free base or in the form of pharmaceutically acceptable addition salt, in particular the bimaleate salt, as well as pharmaceutical compositions containing said compound. In literature, the compound is also known under code LEK-8829. More particularly, present invention relates to a novel method of treatment for reduction of abstinence symptoms after cocaine withdrawal and for suppression the symptoms of craving for cocaine withdrawal and for suppression the symptoms of craving for cocaine reinforcement, and to the use of said active substance for the preparation of the pharmaceutical composition for the treatment of cocaine addiction. In addition to the treatment of cocaine addiction, the present invention also relates to the method for treatment of the addiction with amphetamine, methamphetamine, dextroamphetamine, 3,4-methylenedioxymethamphetamine and pemoline or acid addition salts thereof.

9 Claims, 3 Drawing Sheets

Figure 1

TREATMENT OF PSYCHOSTIMULANT ADDICTION

FIELD OF THE INVENTION (MPK A 61 K 31/48)

The present invention belongs to the field of pharmaceutical industry and relates to a new method for the treatment of psychostimulant addiction, in particular cocaine addiction, that is, to new use of 9,10-didehydro-N-methyl-N-(2-propynyl)-6-methyl-8β-aminomethylergoline or pharmaceutically acceptable acid addition salts thereof, the compound known under code LEK-8829, as well as pharmaceutical compositions containing this compound. More particularly, the present invention relates to the method of inhibiting or eliminating the symptoms of psychostimulant withdrawal, in particular cocaine, in individuals undergoing treatment for psychostimulant abuse with an emphasis on the method of preventing craving for psychostimulants after withdrawal, in particular cocaine, with the use of compound LEK-8829.

TECHNICAL PROBLEM

At present, no effective pharmacotherapy exists for successful treatment of psychostimulant addiction, particularly cocaine; therefore, there is a constant need for new and improved methods for treating psychostimulant addiction.

PRIOR ART

Psychostimulants such as cocaine and amphetamine and their derivatives are the substances which in humans cause euphoria, increase alertness (reduce fatigue) and increase physical capacity. It is now proposed that the primary site of the action of psychostimulants is the mesolimbic and mesocortical dopaminergic system. Active substances increase the dopaminergic transmission at first, but long-term administration results in a reduction of the dopaminergic activity and, consequently, produces dependence. Increased dopaminergic activity in case of cocaine is primarily due to inhibition of the activity of the membrane transport protein which eliminates physiologically released dopamine from the synaptic cleft. Amphetamine acts mainly by causing massive release into the synaptic cleft. In addition, it is also a potent monoamine oxidase inhibitor and thus an inhibitor of extracellular metabolism of dopamine.

Literature, however, reports about the trials for the treatment of psychostimulant addiction, that is cocaine addiction but, at present, no effective pharmacotherapy exists for the treatment of psychostimulant addiction.

U.S. Pat. No. 5,075,341 describes a method for the treatment of cocaine dependence with buprenorphine.

U.S. Pat. No. 4,935,429 discloses a method for the treatment of psychostimulant addiction, particularly cocaine, with dopamine agonists, in particular with pharmaceutically acceptable ergot alkaloids as dopamine agonists, preferably with bromocriptine.

Cocaine and acid addition salts thereof, such as hydrochloride salt, are well known as psychostimulants. The chemical structure of cocaine is disclosed, for example, in The Merck Index, An Encyclopedia of Chemicals, Drugs, and Biologicals, $13^{Ed}$, 2001, under Monograph number 2480.

Bromocriptine and acid addition salts thereof, such as, for example, metasulphonic acid, is known as a prolactin inhibitor and an antiparkisonian and is disclosed in The Merck Index under pod Monograph number 1400.

L. Handelsman et al, Am. J. Addict 1997, Vol 6 (1), 54-64 report that in spite a initial promising pilot studies, in recent studies bromocriptine has not proved useful to reduce cocaine use in cocaine-dependent or cocaine craving persons. These studies of the treatment of cocaine addiction with bromocriptine were limited to the use of low doses of bromocriptine, to 7.5 mg daily.

DESCRIPTION OF THE INVENTION

The objective of the present invention is to develop a new and improved method for the treatment of psychostimulant addiction, particularly cocaine or pharmaceutically acceptable acid addition salts thereof, with a medicament which would act as an antidote against acute (toxic) effects of cocaine overdosage to block euphoric effects of cocaine and which would relieve the abstinence syndrome after cocaine withdrawal in cocaine addicts thereby preventing craving for cocaine reinforcement.

This problem has been solved by the present invention which relates to the new method for the treatment of cocaine addiction with the use of 9,10-didehydro-N-methyl-N-(2-propynyl)-6-methyl-8β-aminomethylergoline or pharmaceutically acceptable acid addition salts thereof of formula:

The substance acts as a partial dopamine agonist and may be used in the form of free base or in the form of its pharmaceutically acceptable acid addition salt. A pharmaceutically acceptable acid addition salt may be prepared by reaction of said substance in the form of free base with physiologically acceptable organic or inorganic acids such as acetic, formic, maleic, tartaric, citric, metasulphonic, hydrobromic, hydrochloric, sulphonic acid and the like. The preferred salt of the said substance is the bimaleate salt which in said case may also be used in diastereomeric forms or racemates.

The compound 9,10-didehydro-N-methyl-N-(2-propynyl)-6-methyl-8β-aminomethilergoline is known from U.S. Pat. No. 5,288,724 in which the new ergoline derivatives of 2-propynylamine with antidepressant and anxiolytic action are protected.

U.S. Pat. No. 5,480,885 of the same authors discloses a method for the treatment of psychoses with an antipsychotic effective amount of ergoline derivatives of 2-propynylamine.

The article of I. Krisch, The Journal of Pharmacology and Experimental Therepeutics, 1994, Vol. 271 (1), 343-352, describes the pharmacological studies of the new ergoline derivative of 9,10-didehydro-N-methyl-N-(2-propynyl)-6-methyl-8β-aminomethyergoline as a potential antipsychotic, coded LEK-8829 and represented by the chemical structural formula.

Further in the description of the present invention the code LEK-8829 is used for the compound 9,10-didehydro-N-methyl-N-(2-propynyl)-6-methyl-8β-aminomethylergoline and pharmaceutically acceptable acid addition salts thereof, respectively.

We have found that in a number pharmacological model in experimental animals the compound coded LEK-8829 was effective in the way leading to a conclusion about its potential usefulness in the treatment of cocaine addiction in humans.

In our opinion, active substance LEK-8829 and pharmaceutically acceptable acid addition salts thereof, in addition to treating cocaine addiction in humans, may also be suitable for the treatment of addiction with other psychostimulants, such as amphetamine, methaphetamine, dextroamphetamine, 3,4-methylenedioxymethamphetamine and pemoline.

On the basis of the known hypothesis of a separate role of dopamine $D_2$ and dopamine $D_1$ receptors, respectively, in developing cocaine addiction and the results of testing in a number of pharmacological models in experimental animals which showed antagonistic effects of LEK-8829 on dopamine $D_2$ receptors and agonistic effects on dopamine $D_1$ receptors; we used the model of craving, that is, the "within session extinction and reinstatement" paradigm in the cocaine self-administration model in the experiment in rats and tested if LEK-8829 may prevent reinstatement of self-injecting. The effect of LEK-8829 (in the form of bimaleate salt) was compared with the effect of bromocriptine (in the form of methanesulphonic salt), cocaine was used in the form of hydrochloride salt in the experiments in rats.

We have unexpectedly found that active substance LEK-8829 proportionately to the dose used inhibited or prevented reinstatement of self-administration, but bromocriptine did not have such effect. On the basis of the experiments in experimental animals it is found that LEK-8829 would be useful for reduction of cocaine-craving symptoms in human cocaine addicts after a prolonged cocaine-free period. Since data from the literature do not support the hypothesis that bromocriptine prevents a relapse of cocaine-craving, as reported by H. R. Krancler and L. O. Bauer in their article, Br. J. Addict. 1992, Vol. 11, 1537-1548, in our opinion the active substance LEK-8829 would be an improved medicament with regard to known bromocriptine. The said finding has been truly unexpected and surprising.

A bell-shaped curve in the ratio available cocaine dose/rate of cocaine self-administration in experimental animals, as described, for example, by F. I. Carrol et al, J. Med. Chem. Vol. 42, no. 15, 2721-2736 (1999), "Pharmacotherapies for Treatment of Cocaine Abuse: Preclinical Aspects" is well known. By the new method of treatment of the present invention, we achieved a reduction of the ascending limb of the curve in the ratio the dose/input of cocaine as well as a reduction in case of the largest available cocaine dose on the descending part of the curve. Insofar known and proposed medicaments and active substances, respectively, for the treatment of psychostimulant addiction, particularly cocaine, have not produced the desired reduction of said bell-shaped curve which may be the measure for treatment effectiveness of psychostimulant addiction, such as cocaine. The said finding, which also presents a novel and significant improvement of the treatment of psychostimulant addiction, particularly cocaine in humans with the compound LEK-882 has proved to be unexpectedly effective as well.

The active substance LEK-8829 of the present invention may be used orally or parenterally as such or as a composition comprising conventional pharmaceutical carriers or excipients. It may be used orally in the form of tables, dispersion powder granules, capsules, syrups or elixirs, or parenterally in the form of solutions such as, for example, sterile injections of aqueous solution. Tablets may contain the active substance together with conventional pharmaceutically acceptable excipients such as, for example, inert diluents and granulating, disintegrating and lubricating agents. Tablets may be uncoated or coated by known techniques for slow disintegration and absorption in the gastrointestinal tract thus providing a sustained action for an extended period of time. Suspensions, syrups and elixirs may contain the active substance together with conventional excipients. Capsule may contain the plain active substance or admixed with solid inert diluents. Injection formulations may be prepared by known techniques and contain the active substance together with a carrier or excipient.

The dose unit in the pharmaceutical compositions of the present invention contains from 0.001 to 20 mg of LEK-8829, preferably from 0.1 to 5.0 mg, in the form of free base or pharmaceutically acceptable acid addition salts thereof.

The present invention also relates to the use of the active substance LEK-8829 and pharmaceutically acceptable acid addition salts thereof for production of the pharmaceutical composition for the treatment of cocaine addiction.

The present invention is illustrated but in no way limited by the following samples:

EXAMPLE 1

Effects on Locomotor Activity

In the experiments in eight mice, intraperitoneal injection of LEK-8829 (in the form of bimaleate salt) inhibited the increased locomotor activity produced by intraperitoneal cocaine injection of 20 mg/kg. The inhibitory effect was dose dependent ($ID_{50}$=1.2 mg/kg). Although LEK-8829 also inhibited the spontaneous locomotor activity ($ED_{50}$=2.1 mg/kg), the ratio of $ED_{50}/ID_{50}$, that was 1.8, suggested partial selectivity of the effect against cocaine.

EXAMPLE 2

Drug Discrimination Studies

In the experiments in six rats LEK-8829 (in the form of bimaleate salt) at doses of 0.25 to 2.5 mg/kg did not replace the discriminative stimulating effect of cocaine at dose of 10 mg/kg. On the other hand, in the same model, that is, in six rats, LEK-8829 (in the form of bimaleate salt at doses of 0.5 to 5 mg/kg partly inhibited the discriminative stimulating effect of cocaine at dose of 10 mg/kg. Partial antagonism of cocaine effect (56%) occurred at dose of 2.5 mg/kg. Discriminative stimulating effects of LEK-8829 (in the form of bimaleate salt) at doses of 0.032 to 0.32 mg/kg were also tested in four *Rhesus* monkeys that were trained to distinguish cocaine (0.4 mg/kg) from the physiological saline. Like rats, the monkeys did not recognize the discriminative stimulating effect of plain LEK-8829 in the sense of cocaine effect but they also did not discriminate the effect of LEK-8829 from the effect of the physiological saline. According to the data from literature, it is well known that rodents and primates are capable to discriminate most psychostimulants abused by humans. Therefore, a model of the specific drug discrimination in experimental animals is a suitable method for the assessment of new active substances in case of the abuse of psychostimulants. The results of the presented study indicate that LEK-8829 has no addictive potential as exhibited by cocaine but it prevents the effects of cocaine.

EXAMPLE 3

Studies in Animal Models of Cocaine Self-Administration

The action of the active substance LEK-8829 (in the form of bimaleate salt) at doses ranging from 0.25 to 2.5 mg/kg on sensations of pleasure induced by cocaine self-administration was assessed as the effect on the rate of cocaine self-administration in the experiments in five rats. For determination of the specificity of the effect on cocaine, a solution of saccharin was used as a comparative stimulant. LEK-8829 in the dose range from 0.2.5 to 1.55 mg/kg produced a right shift of the curve in the ratio dose/response to cocaine (four of five animals), and also decreased the height of the curve in one animal. In the range of medium doses, LEK-8829 caused an increase in overall input of cocaine self-administration in three animals. The results indicate that LEK-8829 blocks euphoric stimulating effect of cocaine. LEK-8829 also influenced the input of saccharin (non-specific effect), however, compared to the effect on cocaine ($ED_{50}$=0.17 mg/kg), the blocking effect of LEK-8829 on the input of saccharin is evident at higher doses ($ED_{50}$=2.16).

The effect of LEK-8829 (in the form of bimaleate salt) at doses of 0.032 to 0.32 mg/kg intramuscularly on cocaine self-administration in comparison with the effect on food intake (specificity of the effect on feelings of pleasure induced by cocaine, in comparison with non-specific sedative effect) was also tested in four Rhesus monkeys. LEK-8829 inhibited cocaine self-administration; the effect was dose-dependent. At small and medium doses (0.032 and 0.1 mg/kg) LEK-8829 decreased the ascending part of the curve in the ratio dose/input of cocaine; likewise, it also decreased input case at largest available cocaine dose (0.3 mg/kg inj.) on the descending part of the curve. At the largest dose (0.32 mg/kg) LEK-8829 blocked the effect of cocaine along the entire (ascending and descending) part of the curve in the ratio dose/input of cocaine (see F. I. Carrol et al, J. Med. Chem., Vol. 42, no. 15, 2721-2736, (1999)). LEK-8829 exhibited only a minor inhibiting effect on food intake. The results indicate the specific effect LEK-8829 against cocaine action.

EXAMPLE 4

Comparative Testing of the Compound LEK-8829 and Bromocriptine in the Craving Model in the Rats Self-Administering Cocaine Introduction Cycle of Addiction The development of drug dependence (psychostimulants, opiates) involves those structures of the brain which are important for motivation and for experiencing the sensation of pleasure—the reward system of the brain (Dackis and O'Brien, 2001). Psychomotor stimulants are addictive drugs because they produce sensations of pleasure and at the same time reinforce the behaviour leading to drug reinforcement. In case of recreational drug use the cycle of addiction may be defined with two types of behavioural patterns. The "appetitive" behaviour is characterized by drive (motivation) to ingest the drug and is manifested as psychomotor restlessness before the ingestion, while the "consummatory" behaviour is marked by drug intake and the symptoms and subjective descriptions of intense feelings of pleasure (euphoria) immediately after ingestion. Euphoria thus acts as a reward and reinforces the behaviour that has led to drug intake (positive reinforcement). The physiological processes on which appetitive and consummatory behaviour is based and which lead to the reward are called proponent processes.

Spiraling Distress

The cycle of addiction could progress into a spiraling distress; the latter is characterized by the failure of control mechanisms that regulate the input of a drug into the body (Ahmed et al, 2002). Pleasure on chronic drug-intake decreases while the desire for repeated drug use increases. This is manifested as an increase in the dosages and frequency of drug use (development of tolerance). Negative conditioning additionally increases the desire to ingest the drug again; this is based on a range of unpleasant psychophysical sensations (dysphoria) that accompany drug withdrawal and may lead to the development of withdrawal syndrome in chronic drug users. Withdrawal of the drug exposes the so-called drug-opponent processes that were established to counteract chronic presence of the drug in the brain. Dysphoria is particularly strong after chronic use of opiates, in which drug withdrawal causes numerous unpleasant vegetative symptoms as a result of drug-opposing processes in the brainstem. In persons addicted with psychostimulants, psychological dependence is what primarily develops. Psychological dependence is based on neurochemical adaptation (plasticity) of the brain's reward system (Weiss et al, 2001, Shalev et al, 2002). Intense craving for the drug after its withdrawal is manifested in a reduced variability of behavioural patterns in favour of an uncontrollable repetition of the behaviour related to drug use (compulsive behaviour).

Pathophysiological Basis of Cocaine Dependence

The basis for the failure of control mechanisms which regulate the input of cocaine in the body is plastic adaptation in the brain's reward system. Cocaine inhibits the dopamine transport protein, impeding the uptake of released dopamine into presynaptic nerve endings, thus increasing dopamine concentration in dopamine synapses (Wise, 1984). Activation of a dopaminoceptive pathway of the reward system is involved in the establishment and expression of appetitive behavioural patterns (related to cocaine-seeking) and in the establishment of consummatory behaviour patterns which the subject experiences and expresses as a surge of pleasure in cocaine rush (Withers et al, 1995). A surge of pleasure in cocaine rush is probably followed by a short-term period of reduced activity of the neuronal pathways that were activated during ingestion (the rebound effect). During chronic drug use, the response of nerve transmission involved in consummatory behaviour to dopamine may gradually diminish (tolerance). Therefore, in order to achieve the same reward, that is pleasure of the same intensity, increased input of cocaine is necessary. On the other hand, the nerve transmission involved in the expression of appetitive behavioural patterns (related to drug-seeking) probably becomes more responsive to dopamine. However, this may not be contradiction in a response of the dopaminergic system so since increased or reduced responses to dopamine are probably transmitted via two different dopaminoceptive pathways of the brain's reward system which thus enables discrimination in responding to stimulants which trigger appetitive or consummatory behaviour (Mc Farland and Kalivas, 2001).

Concerning the development of cocaine dependence, some researches tend to put a greater emphasis on the significance of negative conditioning due to dysphoria which occurs as a result of the opposing neurochemical processes in the brain reward system. Anhedonia which develops after withdrawal of the chronic use is related to dopaminergic hypoactivity as a result of the damage of the dopamine neurons during the chronic use (the damage due to toxic effects of the excessive dopamine activity).

Extinction and Reinstatement

Successful detoxification and extinction of behavioural patterns and symptoms related to cocaine use and its withdrawal is followed by a prolonged period during which there is a greater probability of reinstatement of cocaine-seeking behaviour. The withdrawal period is characterized by anergy, anhedonia, depression, anxiety and irritability. It is supposed that some of these symptoms are based on long-term neurochemical adaptation leading to reduced response of the brain's reward system for dopamine. During the period of abstinence proponent processes easily induce the craving for cocaine; all of them have one thing in common—they lead to an increased dopamine concentration in the brain's reward system. This, for example, occurs during stress, may be induced by environmental cues associated with cocaine use and upon failure of self-control (e.g., the ingestion of a relatively small dose of cocaine) (Spealman et al, 1999). The effect of stress on the reinstatement is complex; it may be at least partly explained by the release of dopamine in the nucleus accumbens. Stress-associated mediator is corticotropin releasing hormone (CRH); the latter may induce the release of dopamine in the nucleus accumbens. The fact that cocaine-craving can be induced by environmental stimuli associated with the use of cocaine indicates the involvement of the brain areas involved in memory (hippocampus, amygdale). The activation of these areas via direct or indirect associations can also trigger the release of dopamine in the nucleus accumbens. Likewise, in a single failure of self-control, cocaine indirectly, via an increased synaptic concentration of dopamine in the nucleus accumbens, may trigger a relapse of the compulsive behaviour which has developed in the period of cocaine dependence (Koob et al, 2001).

The Role of Dopamine $D_1$ and $D_2$ Receptors in the Development Cocaine Dependence In an attempt to understand the role of dopamine receptors in the development of cocaine dependence, the results of studies are interesting that speak in favour of separate locations and separate roles of dopamine $D_1$ and $D_2$ receptors in the development and maintenance of dependence (Khroyan et al, 2000). Some researches postulated the hypothesis that the activation of $D_2$ receptors in the core of the dopaminergic nucleus of the brain's reward system (the nucleus accumbens) has a positive association with the appetitive behaviour, while the activation of $D_1$ receptors has a positive association with the consummatory behaviour in the cycle of addiction (Self's hypothesis) (Self et al, 1996; Self, 1998). These researches believe that dopaminoceptive pathways that are associated with the activity of dopamine $D_1$ receptors (mainly located in the shell of the nucleus accumbens) are desensitized after long-term cocaine use, and dopaminoceptive pathways that are associated with the activity of dopamine $D_2$ receptors (mainly found in the core of the nucleus accumbens) are sensitized. The sensitization of the appetitive behaviour and the development of tolerance to cocaine may be the consequence of permanent changes in responses of the nucleus accumbens.

Possibilities of the Prevention of Reinstatement of Cocaine Dependence by Pharmacological Action on the Dopamine Receptors On the basis of the abovementioned dopaminergic theory, hypotheses have been postulated that the reinstatement of cocaine-seeking behaviour could be prevented by using antagonists or agonists of dopamine receptors. For example, according to Self's hypothesis, the antagonists of dopamine $D_2$ receptors could inhibit appetitive behaviour, while the agonists of dopamine $D_1$ receptors would mimic the cocaine stimulus and through satiation of reward pathways diminish the drive for cocaine ingestion. However, it turned out that dopamine $D_2$ antagonists (substances with antipsychotic activity) may be unsuitable for the prevention of cocaine craving as they are known to produce aversive effects (Self et al, 1996). Preclinical studies with bromocriptine, an agonist of dopamine $D_2$ receptors, did not yield the desired results either. Bromocriptine did not prevent the relapse to cocaine dependence, and at certain doses it even caused a relapse itself or proved to be addictive (Wise et al, 1990). Reports of pilot clinical studies with bromocriptine were initially very promising since, according to subjective reports of cocaine addicts, it somewhat alleviated the symptoms of intense craving for cocaine during the withdrawal period. Unfortunately, subsequent more extensive studies showed that this effect was not statistically significant (Handelsman et al, 1997). The results of preclinical studies are also interesting showing that a relapse reinstatement of cocaine dependence might be prevented both with agonists and antagonists of dopamine $D_1$ receptors (Khroyan et al, 2000). It could be therefore concluded that pharmacological prevention as well as pharmacological substitution for the cocaine stimulus reduce the desire for cocaine ingestion.

Properties of 9,10-didehydro-N-methyl-N-(2-propynyl)-6-methyl-8β-aminomethylergoline (LEK-8829) and Acid Addition Salts Thereof Previous studies have shown that LEK-8829, a potential atypical antipsychotic (Krisch et al, 1994), has antagonistic effects on $D_2$ receptors and agonist effects on $D_1$ receptors ( Zivin et al, 1996; Zivin et al, 1998, Sprah et al, 1999). We have found that in the basal ganglia of rats LEK-8829, via stimulation of the neuronal pathways expressing $D_1$ receptors, may modulate (reduce) hypokinetic effects conferring the blockade of the neuronal pathways expressing $D_2$ receptors (Glavan et al, 2002). Because of its agonistic effects on dopamine receptors, LEK-8829 was also proposed for use as an antipsychotic with greater efficacy in the treatment of negative symptoms of schizophrenia and as an antipsychotic, respectively, because of its smaller tendency to cause parkinsonism. Similar thinking regarding the potential advantages has been lately proposed for some other non-ergoline substances with simultaneous agonistic effects on $D_2$ receptors and antagonistic effects on $D_1$ receptors (Jin et al, 2002). On the other hand, we have also proposed that LEK-8829 may potentially be useful as an antiparkinsonic drug with a smaller tendency than, for example, bromocriptine to cause psychotic behaviour (Zivin et al, 1998).

Aim of the Study and Hypothesis

The aim of the study was to explore the efficacy of LEK-8829 in preventing the cocaine-induced reinstatement of self-administration behaviour in a rat model of "within the session extinction and reinstatement" paradigm, and to compare the effect of LEK-8829 with that of bromocriptine.

Our hypothesis was based on Self's hypothesis for a separate role of dopamine $D_2$ and $D_1$ receptors, respectively, in the development of cocaine dependence, and on previous results that had indicated potential antagonistic effects of LEK-8829 on brain systems expressing dopamine $D_2$ receptors and agonistic effects of LEK-8829 on brain system expressing dopamine $D_1$ receptors. We have postulated the hypothesis according to which LEK-8829 with antagonistic effects on dopamine $D_2$ receptors inhibits the appetitive behavioural patterns associated with cocaine-seeking, while with agonistic effects on dopamine $D_1$ receptors imitates the cocaine stimulus thus satiating the consummatory component of cocaine-reinforcement.

Materials and Methods

Animals

The study was performed in male Wistar rats (*Rattus norvegicus*) (the number is given above the columns in the figures) each weighing 180 to 210 g at the beginning of the experiment. The animals used in this experiment were maintained on a 12-hour dark-light cycle under controlled conditions at temperature 22 to 24° C., individually housed in standard cages with free excess to food and water.

Drugs

In the tests the following active substances were used:
Cocaine hydrochloride
Bromocriptine mesylate
LEK-8829 (9,10-didehydro-N-methyl-N-(2-propynyl)-6-methyl-8β-aminometylergoline bimaleate)

Operant Cage for Self-Injecting

The rats were trained and tested in standard operant test chambers (Coulbourn Instruments, Allentown, Pa., USA). Test chambers were built in a modular form and placed in sound-attenuated cubicles. Each was equipped with a ventilating fan that also served as sound source to mask external sound. Chambers were equipped with bulbs emitting white lights. Each chamber contained two nose-poke operanda mounted in 2 cm from the floor and 10 cm apart on the same wall. The left nose-poke operandum was active, the right one inactive. Each activation of the active nose-poke operandum resulted in an intravenous infusion of 0.110 ml of physiological saline containing 0.22 mg/kg of cocaine over 2 seconds. The cocaine solution was administered via the catheter. The latter connected the rat to a syringe (10 water electric pump (RAZEL, model A, 10 rpm), installed outside the cage. Time schedule of the experiments and data acquisition were controlled by a computer operated by a software package (Graphic State Notation 2 2.002-00; Coulbourn Instruments, Allentown, Pa., USA).

Implantation of the Catheter

Each rat was anesthetized with the anaesthetic mixture (ketamine 60 mg/kg and xylazine 8 mg/kg) and implanted with an indwelling jugular catheter. The catheter was composed of silastic internal part (30 mm; Dow Corning Corporation, Midland, Mich., USA) and a renathane external part (90 mm; Braintree Scientific Inc., Braintree, Mass., USA), inner diameter 0.5 mm and outer diameter 1.0 mm. The silastic inert part of the catheter was inserted through the right jugular vein into the right atrium, and fixed to the jugular vein with a single stitch and with another stitch to the underlying neck muscle. The external part of the catheter was passed subcutaneously to exit the animal back, and at the exit the catheter was stoppered with an adapted needle, outer diameter 0.7 mm (Microlance 3, 22G2; BD Medical systems, Drogheda, Ireland). In order to maintain its patency, the catheter was infused daily with a mixture of the antibiotic and the antithrombotic agent (gentamicin 12 mg and heparin 500 IU per 100 ml of physiological saline). After catheter implantation, the animals were left to recover for seven days before starting with further tests. The patency of the catheters was occasionally checked by injecting the anesthetic solution through the catheter. Within 3 seconds of the injection, the animals with an intact catheter lost consciousness for a few seconds. In rats with a damaged catheter, a new one was inserted into the left jugular vein.

Self-Administration Training

The rats were trained in self-injection of cocaine in daily, 2-hour self-administration sessions during their light cycle, every day except on Saturdays and Sundays. At the beginning of each session, the light in the cage was switched on and an automatic injection of a cocaine dose (0.22 mg/kg) was delivered. Each time the active nose-poke operandum was activated, a yellow light was switched on inside the active opening, an intravenous injection of 0.22 mg of cocaine/kg in 0.110 ml of physiological saline was delivered over two seconds (a fixed ratio (FR)–1). The yellow light remained lit throughout the injection. Each activation of the active opening was followed by a 30-second period of inactivation (timeout period when the light in the cage was switched off and activation of the active opening was only recorded but without any consequences). Activation of the inactive opening was also recorded but it did not trigger any consequences (it served as control). The criterion to learn the self-injection procedure was at least 30 activations of the active nose-poke operandum during a 2-hour session and the ratio of activations of active to inactive opening of at least 3:1. Self-administration was stable when the criterion was achieved at least on three consecutive days.

Test Protocols

The "within session extinction and reinstatement" paradigm was used. Rats were tested in daily 4-hour self-administration sessions. Throughout the 4-hour session, the test protocol was the same as during the training procedure. During the first two hours, the rats received a cocaine solution upon activation of the active poke nose operandum, and during the second two hours the cocaine solution was replaced with physiological saline. The rats thus gradually learnt that in the last two hours cocaine was no longer available; therefore, during the last two hours the number of activations of the active opening decreased with the time (extinction). The test sessions were repeated until the rats achieved the extinction criterion in the last hour (maximum five activations of the active opening during the last hour of the session). Once the rats had achieved the extinction criterion for the three consecutive days, in the next 180-minute session (in the second part of the test in which the effects of intravenously administered LEK-8829 and bromocriptine after 210 minutes were tested) cocaine was injected into the catheter (2 mg/kg in 0.6 ml of physiological saline) thus inducing a relapse again with priming cocaine injection (activation of the active nose poke operandum). One group of rats (N=9) received various doses of LEK-8829 intraperioneally (for the i.p. injections the animal was carefully taken out of its cage and returned after an injection), the second group (N=6) i.v. (into the catheter). Thirty minutes before a relapse was induced with priming cocaine injection, the rats received various doses of LEK-8829 (the first group i.p. after 150 minutes of the session, the second group i.v. after 180 minutes of the session), bromocriptine (the second group, 2 mg/kg i.v., 60 minutes before priming cocaine injection), or physiological saline (the first group i.p. after 150 minutes of the session, the second group i.v. after 180 minutes of the session). A sequence of the sessions with various protocols was at random. The sessions in which the test substances (LEK-8829, bromocriptine) were tested were always alternated with the sessions in which the animals received only the physiological saline before a relapse was induced with priming cocaine injection. In the group which received the test substances intraperiotoneally, the numbers of activations of the active and inactive nose poke operandi were recorded during the last hour of the session, and in the group which received the test substances intravenously during the last half-hour of the session.

Statistical Analysis

In several rats the intravenous catheter became obliterated before all doses of the test substances could be tested; therefore, the results were analyzed by comparing individual experimental rats. The data (expressed as the number of activations of the active or inactive nose poke operanda during the last hour of the test session for the protocol in which the test substances were administered intraperitoneally and during the last half-hour for the protocol in which the test substances were administered intravenously) were analyzed using unilateral variance analysis (ANOVA) and Scheffe's test.

Results

Approximately half of the experimental animals learnt to self-inject cocaine. A stable level of self-administration was achieved on average in approximately 10-15 sessions. In extinction sessions, all rats achieved the extinction criterion (five extinctions of the active opening at a maximum in the last hour of the session) in on average five sessions. LEK-8829 and bromocriptine were tested only in those rats that had a satisfactory relapse (more than five activations of the active opening in the last hour of the session) in previous sessions after relapse induction with a cocaine injection.

Figure 1:
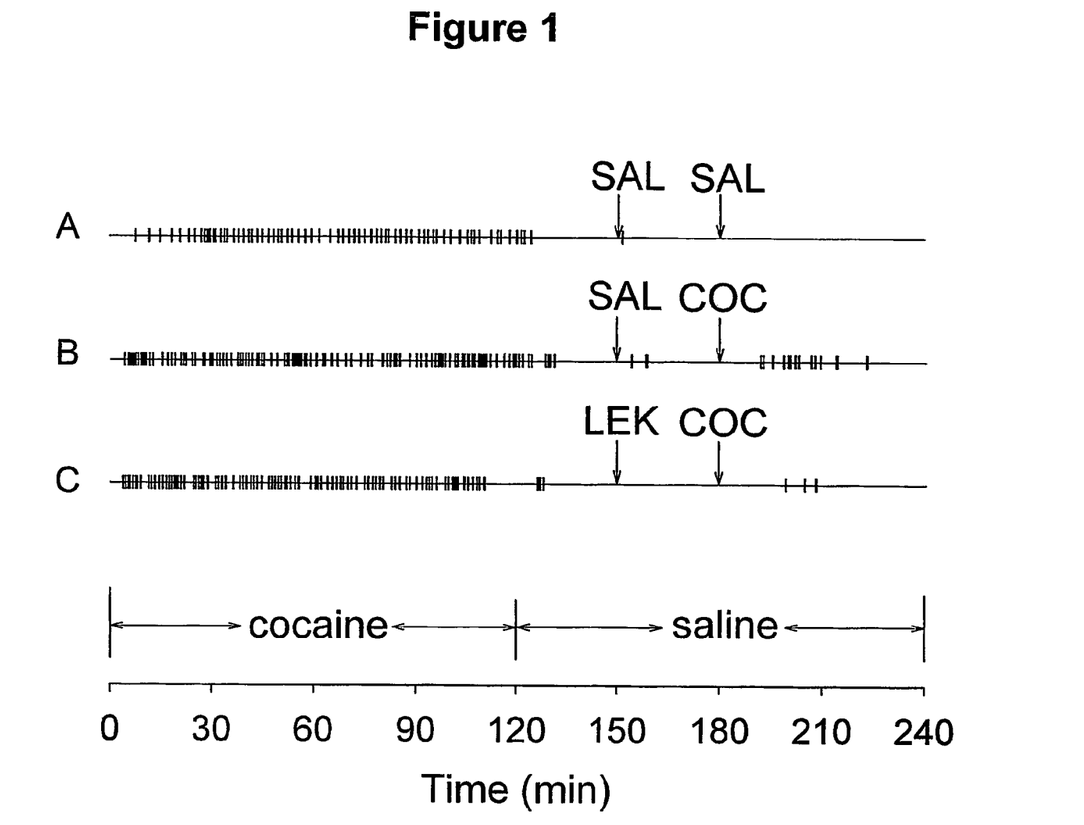

FIG. 1 shows a typical pattern of self-administration in the animals according to protocols A-"extinction", B-"relapse" and C-"relapse prevention" by LEK-8829 pretreatment. A test session lasted 4 hours. During the first two hours the rats received cocaine upon activation of the active nose-poke operandum, and during the last two hours physiological saline. Half-hour later after the replacement of cocaine with physiologic saline solution, the animals were taken out of their cages for a short period of time and injected with either physiologic saline solution i.p. (code: SAL) or LEK-8829 in various doses. Half-hour later (at the start of the last hour of the session) the rats received an i.v. cocaine injection (2 mg/kg; code: COC). LEK-8829 reduced the intensity of self-administration induced by a cocaine injection. The short vertical lines indicate activation of the active nose-poke operandum.

Figure 2:
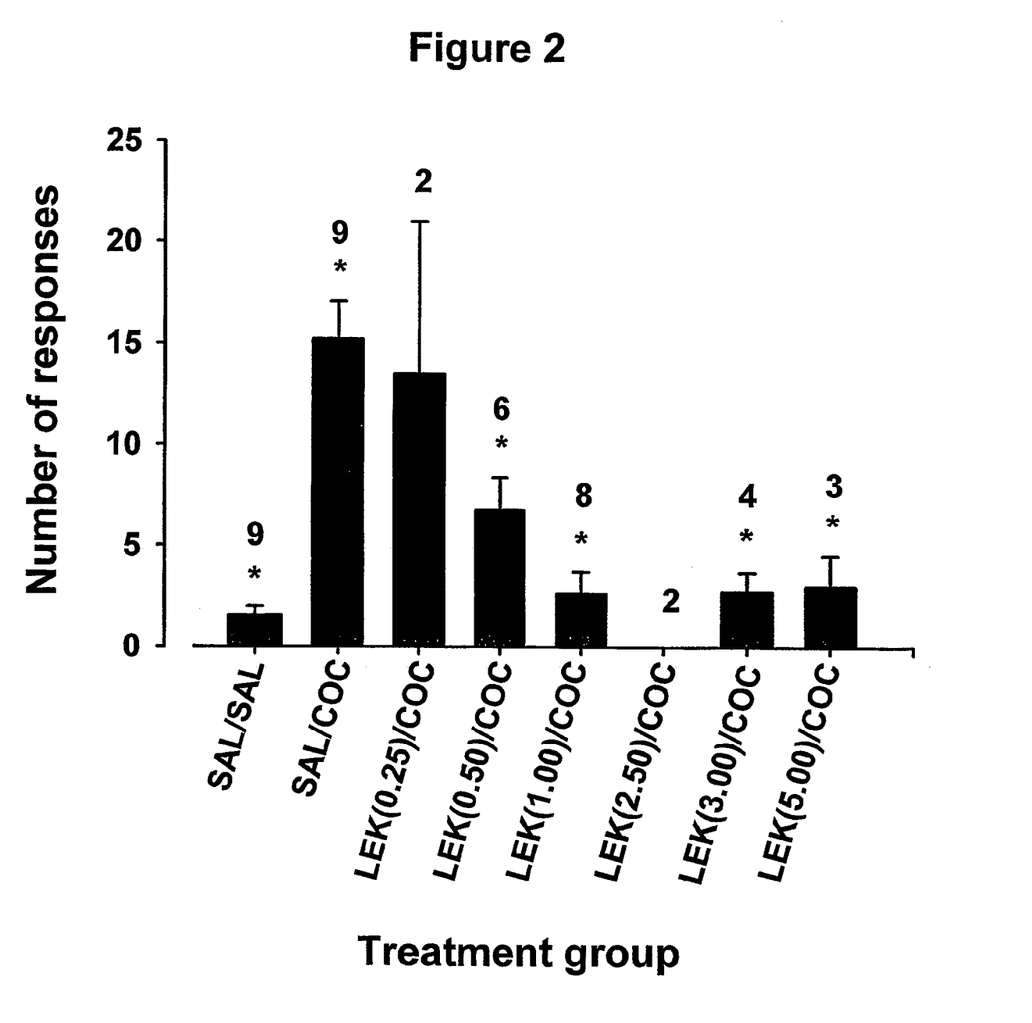

FIG. 2 shows the effects of LEK-8829, injected in various doses intraperitoneally 30 minutes before inducing a relapse with cocaine (2 mg/kg i.v.). LEK at intraperitoneal doses ranging from 0.5 to 5 mg/kg statistically significantly reduced a relapse triggered by cocaine. Each test session lasted 4 hours. In the first half of the session, the responses on the active nose poke operandum were reinforced with cocaine, and in the second half of the session cocaine was replaced with physiological saline. Relapse of drug-seeking was induced with an experimenter deliver cocaine injection (2 mg/kg i.v.). The "within-session extinction" paradigm was used. The data for individual groups are expressed as the average number of activations of the active opening ±SEM during the last hour of the test session (after induction of self-administration with cocaine, 2 mg/kg i.v.). According to the "extinction" protocol, the rats received physiological saline i.p. 150 minutes after the beginning of the session, and then a physiological saline solution i.v. 180 minutes after the beginning of the session (SAL+SAL). According to the "relapse" protocol, the rats received a physiological saline solution i.p. 150 minutes after the beginning of the session, and then a dose of cocaine (2 mg/kg i.v.) 180 minutes after the beginning of the session (SAL+COC). According to the "relapse prevention" protocol, the rats received LEK-8829 in various doses (ranging from 0.25 to 5 mg/kg) 150 minutes after the beginning of the session, and then a dose of cocaine (2 mg/kg i.v.) 180 minutes after the beginning of the session (LEK+COC). The number of activations of the inactive poke nose operandum did no exceed 5% of the number of activations of the active poke nose operandum; data not shown.

Figure 3:
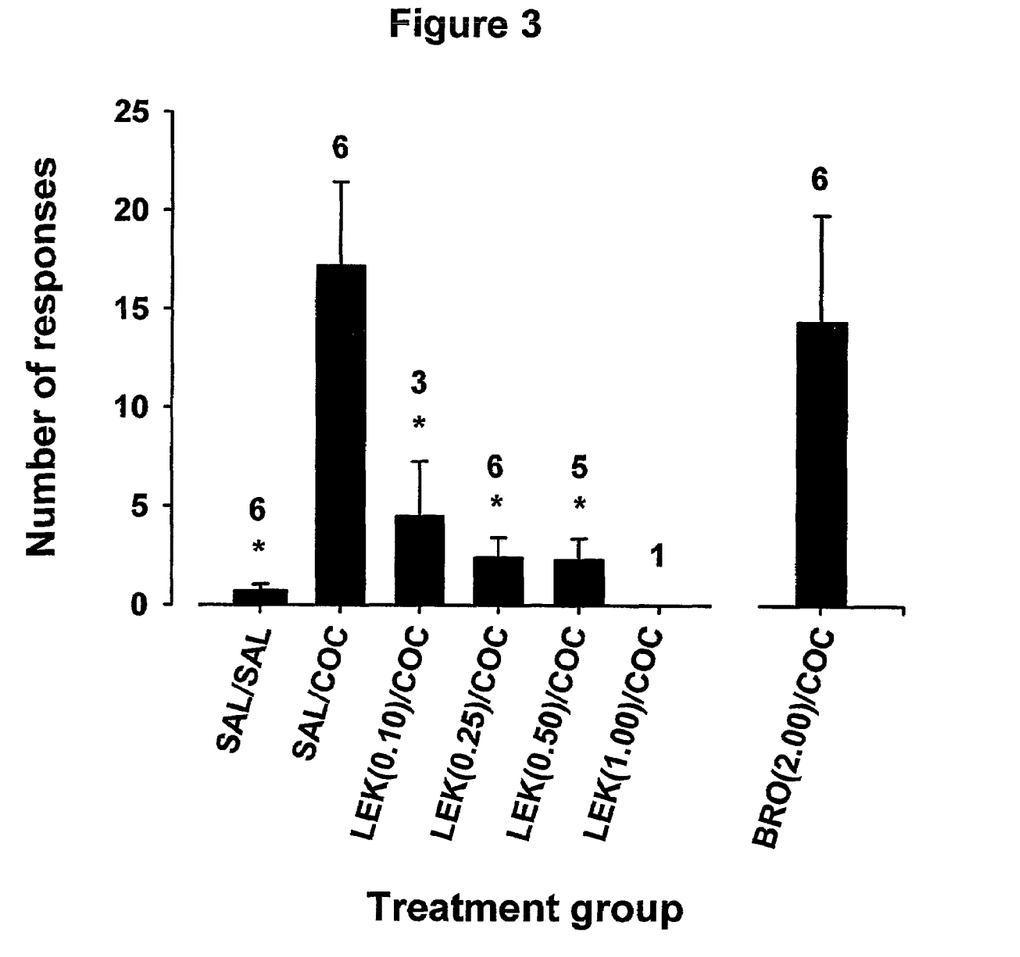

FIG. 3 shows the dose-response effect of intravenous doses of LEK-8829 (30 minutes before inducing a relapse) and the effect of bromocriptine (2 mg/kg, which was also injected intravenously, 60 minutes before inducing a relapse). LEK-8829 at doses 0.25 and 0.5 mg/kg statistically significantly reduced cocaine-induced self-injecting. LEK-8829 at doses 0.1, 0.25 and 0.5 mg/kg also reduced cocaine-induced self-injecting. Bromocriptine at a dose of 2 mg/kg i.v. did not prevent cocaine-induced self-injecting. Each test session lasted 4 hours. In the beginning of the session the response on active poke-nose operandum was reinforced with cocaine for 105 minutes, thereafter to the end of the session cocaine was replaced with physiological saline. Relapse of drug-seeking was induced with an experimenter delivered cocaine injection (2 mg/kg i.v.). The "within-session extinction" paradigm was used. The data are expressed as the average number of activations of the active opening ±SEM during the last half-hour of the test session (after induction of self-administration with cocaine, 2 mg/kg i.v.). According to the "extinction" protocol, the rats received physiological saline solution i.p. 180 minutes after the beginning of the session, and then physiological i.v. 210 minutes after the beginning of the session (SAL+SAL). According to the "relapse prevention" protocol, the rats received physiological saline i.p. 180 minutes after the beginning of the session, and then cocaine (2 mg/kg i.v.) 210 minutes after the beginning of the session (SAL+COC). According to the "relapse prevention" protocol, the rats received LEK-8829 (from 0.1 to 1 mg/kg i.v.) 180 minutes after the beginning of the session, and then cocaine (2 mg/kg i.v.) 210 minutes after the beginning of the session (LEK+COC); or bromocriptine (2 mg/kg i.v.) 150 minutes after the beginning of the session, and then cocaine (2 mg/kg i.v.) 210 minutes after the beginning of the session (BRO+COC). The number of activations of the inactive (control) poke nose operandum did no exceed 5% of the number of activations of the active poke nose operandum; data not shown.

LEGEND

In FIGS. 1, 2 and 3:
statistically significantly lower number of activations of the active nose poke operandum than in the SAL+COC group (unilateral analysis of variance (ANOVA) and Scheff's; $p<0.05$).
SAL, a physiological saline solution: COC, cocaine (in the form of hydrochloride salt); BRO, bromocriptine (in the form of mesylate salt); LEK means LEK-8829, that is, 9,10-didehydro-N-methyl-(2-propynyl)-6-methyl-8β-aminomethylergoline (in the form of bimaleate salt)

CONCLUSION

The results of the study show that 9,10-didehydro-N-methyl-N-(2-propynyl)-6-methyl-8β-aminomethylergoline and pharmaceutically acceptable acid addition salts thereof, in the present invention coded LEK-8829, causes a dose-related reduction of the intensity of cocaine-seeking behaviour induced with a priming cocaine injection in the self-injecting model in rats using the "within-session extinction and reinstatement" paradigm. The results indicate the potential usefulness of the compound LEK-8829 for the prevention of cocaine reinstatement among cocaine addicts during the period of abstinence. The study was based on a hypothesis that LEK-8329 due to its antagonistic effects on dopamine $D_2$ receptors could inhibit the appetitive behaviour which in the said model of self-administration could be interpreted as craving for cocaine while, on the other hand, due to its agonistic effects on dopamine $D_1$ receptors it may mimic the cocaine stimulus, and thus further reduce the drive for cocaine use. We have hypothesized that mimicking a cocaine stimulus may be a significant improvement of LEK-8829 over certain other antipsychotics which due to their antagonistic effects on dopamine $D_2$ receptors induce aversion and thus are less useful for inhibiting the appetitive behaviour. On the other hand, it is well known that bromocriptine, an agonist of dopamine $D_2$ receptors, in the said model can induce appetitive behaviour and may even have additive properties. The study showed that prior treatment with bromocriptine did not prevent appetitive behaviour induced by a cocaine stimulus, and that bromocriptine itself induced the appetitive behaviour. The test sessions lasted 4 hours, and the effects of bromocriptine on cocaine-induced reinstatement of cocaine self-administrated were observed 30 minutes before the end of the session. Bromocriptine was injected 60 minutes before the cocaine injection that induced a relapse for self-administration.

Since the data from literature do not support the assumption that bromocriptine prevents cocaine craving (Kranzler and Bauer 1992), we propose LEK-8829 as an improved or more useful pharmacotherapy for the treatment method of cocaine addiction.

REFERENCE

Ahmed S H et al. Neurobiological evidence for hedonic allostasis associated with escalating cocaine use. *Nature Neurosc* 2002; 5: 625-626

Dackis C A, O'Brien C P Cocaine dependence: a disease of the brain's reward centers. *J Subs Abuse Treat* 2001; 21: 111-117.

Glavan F et al. Modulation of neuroleptic activity of 9,10-didehidro-N-metil-(2-propinil)-6-metil-8-aminometilergoline bimaleate (LEK-8829) by $D_1$ intrinsic activity in hemi-parkinsonian rats. *Mo Pharmacol* 2002; 61: 360-368

Handelsman L et al. Bromocriptine for cocaine dependence. A controlled clinical trial. *Am J Addict* 1997; 6: 54-64

Jin G-H et al. (-) Stepholidine: a potential novel antipsychotic drug with dual $D_1$ receptor agonist and $D_2$ receptor antagonist actions *Trends Pharmacol Sci* 2002; 23:4-7

Khroyan T V et al. Dopamine $D_1$ and $D_2$-like receptor mechanisms in relapse to cocaine-seeking behavior: effects of selective antagonists and agonists. *J Pharmacol Exp Ther* 2000; 294: 680-687

Kranzler H R, Bauer L O. Bromocriptine and cocaine cue reactivity in cocaine-dependent patients. *Br J Addict* 1992; 11.1537-1548

Krisch I et al. Pharmacological studies with two new ergoline derivatives, the potential antipsychotisc LEK-8829 and LEK-8841. *J Pharmacol Exp Ther* 1994; 271:343-352

Mc Farland K, Kalivas, P W. The circuity mediating cocaine-induced reinstatement of drug-seeking behaviour. *J Neurosci* 2001; 21:8655-8663

Self D W. Neural substrates of drug craving and relapse in drug addiction. *Ann Med* 1998; 30:379-389

Self D W et al. Opposite modulation of cocaine-seeking behaviour by $D_1$ and $D_2$ like-dopamine receptor agonists. *Science* 1996; 1586-1589

Shalev U et al. Neurobiology of relapse to heroin and cocaine seeking: a review. *Pharmacol Rev* 2002; 54:1-42

Spealman R D et al. Pharmacological and environmental determinants of relapse to cocaine-seeking behaviour. *Pharmacol Biochem Behav* 1999; 64:327-336

Sprah L et al. Ergoline derivative LEK-8829-induced turning behaviour in rats with unilateral striatal ibotenic acid lesions: interaction with bromocriptine. *J Pharmacol Exp Ther* 1999; 288:1093-1100

Weiss F et al. Compulsive drug-seeking behaviour and relapse. Neuroadaptation, stress, and conditioning factors. *Ann N Y Acad Sci* 2001; 937:1-26

Wise R A. Neural mechanisms of the reinforcing action of cocaine. *NIDA Res Monogr* 1984; 50:15-33

Wise R A et al. Bromocriptine self-administration and bromocriptine-reinstatement of cocaine-trained and heroin-trained lever pressing in rats. *Psychopharmacology (Berl)* 90; 100:355-369

Withers N W et al, Cocaine abuse and dependence. *J Clin Psychopharmacol* 1995; 15:63-78

Zivin M et al. The $D_1$ receptor-mediated effects of the ergoline derivative LEK-8829 in rats with unilateral 6-hydroxydopamine lesions. *Br J Pharmacol* 1996; 119:1187-1196

Zivin M et al. Antiparkinsonian potential of interaction of LEK-8829 with bromocriptine. *Eur J Pharmacol* 1998; 349:151-157

The invention claimed is:

1. A method for treating a psychostimulant addiction, said method comprising administering to an individual in need of such treatment a therapeutically effective amount of 9,10-didehydro-N-methyl-N-(2-propynyl)-6-methyl-8β-aminomethylergoline as a partial dopamine agonist in the form of free base or in the form of pharmaceutically acceptable acid addition salt, wherein the therapeutically effective amount is from about 0.05 to about 20 mg.

2. A method for reducing an abstinence symptom resulting from a withdrawal of a psychostimulant, said method comprising administering to an individual in need of such treatment a therapeutically effective amount of 9,10-didehydro-N-methyl-N-(2-propynyl)-6-methyl-8β-aminomethylergoline as a partial dopamine agonist in the form of free base or in the form of pharmaceutically acceptable acid addition salt wherein the therapeutically effective amount is about 0.05 to about 20 mg.

3. A method for reducing a craving resulting from a withdrawal of a psychostimulant, said method comprising administering to an individual in need of such treatment a therapeutically effective amount of 9,10-didehydro-N-methyl-N-(2-propynyl)-6-methyl-8β-aminomethylergoline as a partial dopamine agonist in the form of free base or in the form of pharmaceutically acceptable acid addition salt wherein the therapeutically effective amount is about 0.05 to about 20 mg.

4. The method according to claim 1, wherein the psychostimulant is selected from the group consisting of cocaine, amphetamine, methamphetamine, dextroamphetamine, 3,4-methylenedioxymethamphetamine, and pemoline, in the form of free base or in the form of a pharmaceutically acceptable acid addition salt.

5. The method according to claim 1, wherein the psychostimulant addiction is cocaine addiction.

6. The method according to claim 2, wherein the psychostimulant is cocaine.

7. The method according to claim 3, wherein the psychostimulant is cocaine.

8. The method according to claim 1, wherein the 9,10-didehydro-N-methyl-N-(2-propynyl)-6-methyl-8β-aminomethylergoline is in the form of a bimaleate salt.

9. The method according to claim 1, wherein the therapeutically effective amount is from 0.1 to 5.0 mg.

* * * * *